United States Patent [19]
Lee et al.

[11] Patent Number: 5,642,433
[45] Date of Patent: Jun. 24, 1997

[54] METHOD AND APPARATUS FOR IMAGE CONTRAST QUALITY EVALUATION

[75] Inventors: Shih-Jong J. Lee, Bellevue; Paul S. Wilhelm, Kirkland, both of Wash.

[73] Assignee: NeoPath, Inc., Redmond, Wash.

[21] Appl. No.: 509,185

[22] Filed: Jul. 31, 1995

[51] Int. Cl.⁶ ................................................ G06K 9/36
[52] U.S. Cl. ................................. 382/199; 382/274
[58] Field of Search .............................. 382/128, 133, 382/168, 199, 256, 257, 274, 286, 308

[56] References Cited

U.S. PATENT DOCUMENTS

| | | | |
|---|---|---|---|
| 3,629,499 | 12/1971 | Carlson | 178/7.2 R |
| 3,721,759 | 3/1973 | Lang | 18/7.2 |
| 3,743,427 | 7/1973 | Weiser | 356/124 |
| 3,824,393 | 7/1974 | Brain | 250/222 PC |
| 3,851,156 | 11/1974 | Green | 235/151.3 |
| 4,000,417 | 12/1976 | Adkisson et al. | 250/201 |
| 4,012,634 | 3/1977 | Bouton et al. | 250/201 |
| 4,045,772 | 8/1977 | Bouton et al. | 340/146.3 B |
| 4,220,850 | 9/1980 | McEachern | 250/204 |
| 4,341,953 | 7/1982 | Sakai et al. | 250/204 |
| 4,349,254 | 9/1982 | Jyojiki et al. | 354/25 |
| 4,352,545 | 10/1982 | Uno et al. | 354/25 |
| 4,577,095 | 3/1986 | Watanabe | 250/201 |
| 4,626,674 | 12/1986 | Oinoue | 250/201 |
| 4,636,051 | 1/1987 | Shippey | 354/402 |
| 4,725,722 | 2/1988 | Maeda et al. | 250/201 |
| 4,810,869 | 3/1989 | Yabe et al. | 250/201 |
| 4,887,125 | 12/1989 | Hideshima | 355/55 |
| 4,991,970 | 2/1991 | Darboux et al. | 356/402 |
| 5,042,077 | 8/1991 | Burke | 382/51 |
| 5,051,770 | 9/1991 | Cornuejols | 354/432 |
| 5,072,382 | 12/1991 | Kamentsky | 364/413.08 |
| 5,091,963 | 2/1992 | Litt et al. | 382/8 |
| 5,107,422 | 4/1992 | Kamentsky et al. | 364/413.08 |
| 5,162,990 | 11/1992 | Odeyale et al. | 364/413.1 |
| 5,204,761 | 4/1993 | Gusmano | 358/461 |
| 5,206,919 | 4/1993 | Keating | 382/46 |
| 5,239,170 | 8/1993 | Hughlett | 250/201.3 |
| 5,257,182 | 10/1993 | Luck et al. | 364/413.1 |
| 5,287,272 | 2/1994 | Rutenberg et al. | 364/413.01 |
| 5,315,700 | 5/1994 | Johnston et al. | 395/163 |
| 5,361,140 | 11/1994 | Hayenga et al. | 358/446 |

OTHER PUBLICATIONS

Bacus, James W. and Les J. Grace, "Optical Microscope System For Standardized Cell Measurements and Analyses", *Applied Optics*, 26:16, pp. 3280–3293, 15 Aug. 1987.

Bartels, Peter H., et al., "A Self–Learning Computer Program for Cell Recognition", *ACTA Cytologica: The Journal of Clinical Cytology*, 14:8, pp. 486–494, Oct. 1970.

Smith, Warren J., "Modern Optical Engineering: The Design of Optical Systems", Copyright ©1966 by McGraw–Hill Book Company, pp. 308–325.

Tanaka, Noboru, et al., "Automated Cytologic Screening System (CYBEST Model 4) : an Integrated Image Cytometry System", Reprinted from *Applied Optics*, vol. 26, No. 16, pp. 3301–3307, Aug. 15, 1987.

Duda, Richard O. and Peter E. Hart, "Fisher's Linear Discriminant", *Patent Classification and Scene Analysis*, Copyright ©1973, pp. 114–119.

Dytch, Harvey E. et al., "An Interactive Microcomputer–Based System for the Quantitative Analysis of Stratified Tissue Sections", *Analytical and Quantitative Cytology and Histology*, vol. 9, No. 1, pp. 69–78, Mar. 1987.

(List continued on next page.)

*Primary Examiner*—Andrew Johns
*Attorney, Agent, or Firm*—Moffa & Associates, P.A.

[57] ABSTRACT

A method for single image based image contrast quality evaluation is used in a computer controlled image system including an automated microscope for acquiring images. An image is acquired. An image contrast score is computed for the image. An image reliability score is computed for the image. The image contrast score and image reliability score are accumulated and combined to produce a contrast quality score. The contrast quality score is compared to a predetermined limit so as to produce a quality of processing result.

16 Claims, 8 Drawing Sheets

OTHER PUBLICATIONS

Weber, J.E. et al., "Fuzzy Reasoning, Possibility Theory and Probability Theory in Expert Systems for Histopathology", Proceedings, 9th Annual IEEE Conference on Engineering in Medicine and Biomedical Sciences, Boston, 1987, pp. 1560–1561.

Wied, G.L. et al., "Expert Systems as Classifiers in Diagnostic Cytopathology", Proceedings, 9th Annual IEEE Conference on Engineering in Medicine and Biomedical Sciences, Boston, 1987, pp. 1915–1917.

Wied, G.L. et al., "Expert System Design Under Uncertainty of Human Diagnosticians", IEEE/Eighth Annual Conference of the Engineering in Medicine and Biology Society, pp. 757–760, ©1986.

Wied, G.L. et al., "Ticas-Stratex, an Expert Diagnostic System For Stratified Cervical Eipthelium", IEEE/Ninth Annual Conference of the Engineering in Medicine and Biology Society, pp. 1557–1559, ©1987.

Serra, J., *Image Analysis and Mathematical Morphology*, pp. 372–423, Academic Press, 1982.

Patten, Jr., Stanley, "Diagnostic Cytopathology of the Uterine Cervix", Basel, Switzerland, Publisher: S. Karger, vol. 3, 2nd Edition in *Monographs in Clinical Cytology*, edited by G.L. Wied, pp. 10–15.

Pattern, Jr., Stanley, "Diagnostic Cytopathology of the Uterine Cervix", Basel, Switzerland, Publisher: S. Karger, 1969, vol. 3, 2nd Edition in *Monographs in Clinical Cytology*, edited by G.L. Wied, pp. 1–9.

Patten, Jr., Stanley, "The Automation of Uterine Cancer Cytology", *Sensitivity and Specificity of Routine Diagnostic Cytology*, Tutorials of Cytology, Chicago, IL, 1976, edited by Wied, Bahr and Bartels, pp. 406–419.

Lundsteen, C., et al., Abstract from *Clin Genet.*, Department of Obstetrics and Gynecology, Rigshospitalet, Copenhagen, Denmark, vol. 45, No. 2, Feb. 1994, pp. 62–66.

Kaplow, L.S., Abstract from *Histochem Cytochem.*, vol. 25, No. 8, Aug. 1977, pp. 990–1000.

METHOD AND APPARATUS FOR IMAGE CONTRAST QUALITY EVALUATION

BACKGROUND OF THE INVENTION

This invention relates to a method for the evaluation of image contrast quality in a single image in an automated optical system. More particularly, the present invention relates to evaluation of image contrast quality in an automated biological screening system, such as a system for analyzing cytological specimens stained according to the Papanicolaou stain process.

In automated optical systems, good image contrast quality promotes good image quality. Good image quality is key to the performance of any imaging application. As a result, it is very important to establish a reliable method to measure image contrast quality of acquired imagery. Such an image contrast quality measure may be used to determine the success of automated image acquisition and may trigger image reacquisition if image contrast quality is not acceptable. Suitable image quality is particularly important for an automated biological specimen screening system. Image contrast quality measurement is, therefore, also important for evaluating performance of such an automated biological specimen screening system.

Therefore, it is a motivation of the present invention to evaluate image contrast quality by measuring the changes in image edge contrast performed on a single image. Measurement of change in image edge contrast is normalized by the edge contrast to achieve image content independence. Additional operations of the present invention further condition the image and remove noise and cluttering to improve the reliability of the image contrast quality measurement.

The image contrast quality measurement employed by the present invention is designed to achieve consistent image contrast quality scoring for a wide range of image contents. It is designed to perform image contrast quality measurement based only on a single image rather than using the relative contrast between multiple images of the same field of view (FOV) acquired at different focus positions. Additionally the invention provides for the utilization of images acquired from biological specimens as well as the utilization of the image contrast scores from all images of a specimen for the evaluation of the processing effectiveness of an automated biological specimen screening system to the specimen.

SUMMARY OF THE INVENTION

The present invention provides a method for single image based image contrast quality evaluation in a computer controlled image system including an automated microscope for acquiring images. At least one single image is acquired. An image contrast score is computed for each of the at least one single image. An image reliablity score is computed for each of the at least one single image. The image contrast score and image reliability score for each single image are accumulated and combined to produce a contrast quality score for each single image. The contrast quality scores of all images from a specimen are combined and compared to a predetermined limit so as to produce a quality of processing result.

Other objects, features and advantages of the present invention will become apparent to those skilled in the art through the description of the preferred embodiment, claims and drawings herein wherein like numerals refer to like elements.

BRIEF DESCRIPTION OF THE DRAWINGS

To illustrate this invention, a preferred embodiment will be described herein with reference to the accompanying drawings.

FIG. 1 comprises FIGS. 1A and 1B which are intended to be pieced together to show one embodiment of an apparatus employed by the invention.

DETAILED DESCRIPTION OF THE PREFERRED EMBODIMENT

The invention provides a method for the measurement of image contrast quality from a single image. It also provides a method to integrate the image contrast quality results from images obtained by an automated biological screening system to evaluate the quality of the processing of a specimen.

In one embodiment of the invention, the system disclosed herein is used in a system for analyzing cervical pap smears, such as that shown and disclosed in U.S. patent application Ser. No. 07/838,064, entitled "Method For Identifying Normal Biomedical Specimens", by Alan C. Nelson, et al., filed Feb. 18, 1992; U.S. patent application Ser. No. 08/179,812 filed Jan. 10, 1994 which is a continuation in part of U.S. patent application Ser. No. 07/838,395, now U.S. Pat. No. 5,528,703 entitled "Method For Identifying Objects Using Data Processing Techniques", by S. James Lee, et al., filed Feb. 18, 1992; U.S. patent application Ser. No. 07/838,070, now U.S. Pat. No. 5,315,700, entitled "Method And Apparatus For Rapidly Processing Data Sequences", by Richard S. Johnston et al., filed Feb. 18, 1992; U.S. patent application Ser. No. 07/838,065, now U.S. Pat. No. 5,361,140 entitled "Method and Apparatus for Dynamic Correction of Microscopic Image Signals" by Jon W. Hayenga et al., filed Feb. 18, 1992; and U.S. patent application Ser. No. 08/302, 355, filed Sep. 7, 1994 entitled "Method and Apparatus for Rapid Capture of Focused Microscopic Images" to Hayenga et al., which is a continuation-in-part of application Ser. No. 07/838,063 filed on Feb. 18, 1992 the disclosures of which are incorporated herein, in their entirety, by the foregoing references thereto.

The present invention is also related to biological and cytological systems as described in the following patent applications which are assigned to the same assignee as the present invention, filed on Sep. 20, 1994 (unless otherwise noted), and which are all hereby incorporated by reference including U.S. patent application Ser. No. 08/309,118 to Conn et al. entitled, "Field Prioritization Apparatus and Method," U.S. patent application Ser. No. 08/309,061 to Wilhelm et al., entitled "Apparatus for Automated Identification of Cell Groupings on a Biological Specimen," U.S. patent application Ser. No. 08/309,116 to Meyer et al. entitled "Apparatus for Automated Identification of Thick Cell Groupings on a Biological Specimen," U.S. patent application Ser. No. 08/098,115 to Lee et al. entitled "Biological Analysis System Self Calibration Apparatus," U.S. patent application Ser. No. 08/308,992 to Lee et al. entitled "Apparatus for Identification and Integration of Multiple Cell Patterns," U.S. patent application Ser. No. 08/309,063 to Lee et al. entitled "A Method for Cytological System Dynamic Normalization," U.S. patent application Ser. No. 08/309,248 to Rosenlof et al. entitled "Method and Apparatus for Detecting a Microscope Slide Coverslip," U.S. patent application Ser, No. 08/309,077, now U.S. Pat. No. 5,566,249, to Rosenlof et al. entitled "Apparatus for Detecting Bubbles in Coverslip Adhesive," U.S. patent application Ser. No. 08/309,931 to Lee et al. entitled "Cytological Slide Scoring Apparatus," U.S. patent application Ser. No. 08/309, 148 to Lee et al. entitled "Method and Apparatus for Image Plane Modulation Pattern Recognition", U.S. patent application Ser. No. 08/309,250 to Lee et al. entitled "Apparatus for the Identification of Free-Lying Cells," U.S. patent application Ser. No. 08/309,117 to Wilhelm et al., entitled "Method and Apparatus for Detection of Unsuitable Conditions for Automated Cytology Scoring."

Figures 1, 1A:
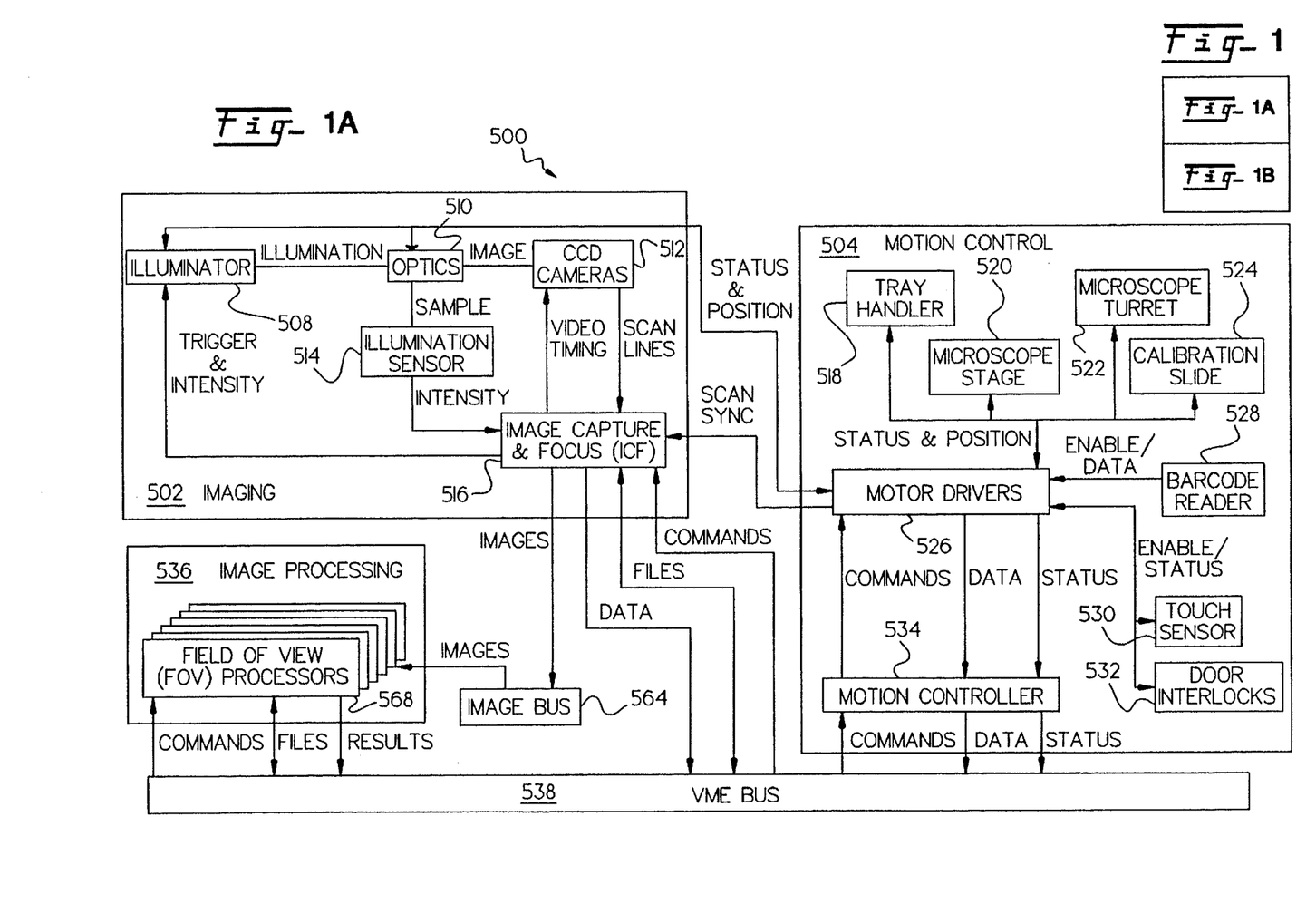
Figure 1B:
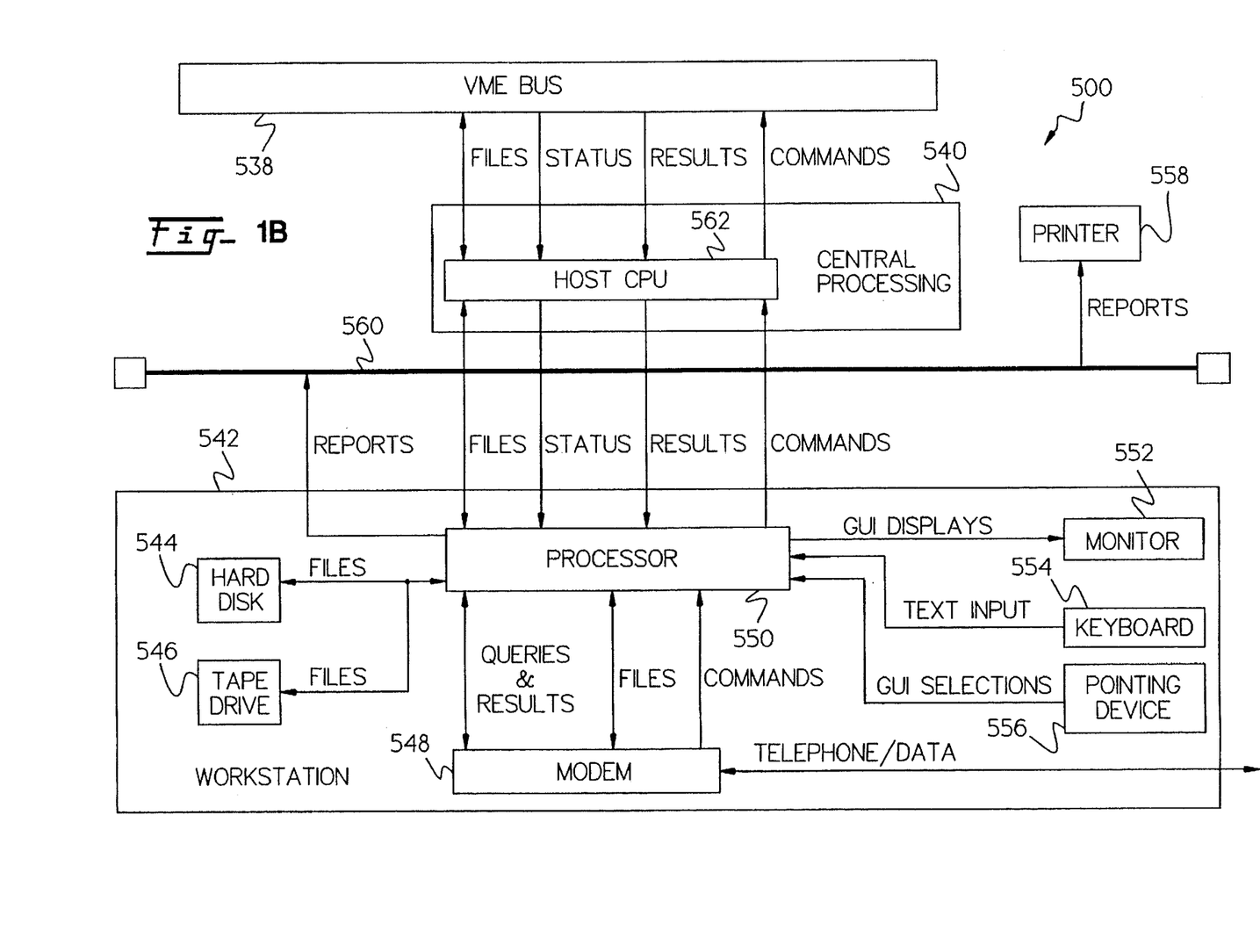

Now refer to FIG. 1 comprising FIGS. 1A and 1B which show a schematic diagram of one embodiment of the apparatus of the invention 500. The apparatus of the invention comprises an imaging system 502, a motion control system 504, an image processing system 536, a central processing system 540, and a workstation 542. The imaging system 502 is comprised of an illuminator 508, imaging optics 510, a CCD camera 512, an illumination sensor 514 and an image capture and focus system 516. The image capture and focus system 516 provides video timing data to the CCD cameras 512, the CCD cameras 512 provide images comprising scan lines to the image capture and focus system 516. An illumination sensor intensity is provided to the image capture and focus system 516 where an illumination sensor 514 receives the sample of the image from the optics 510.

Figure 2:
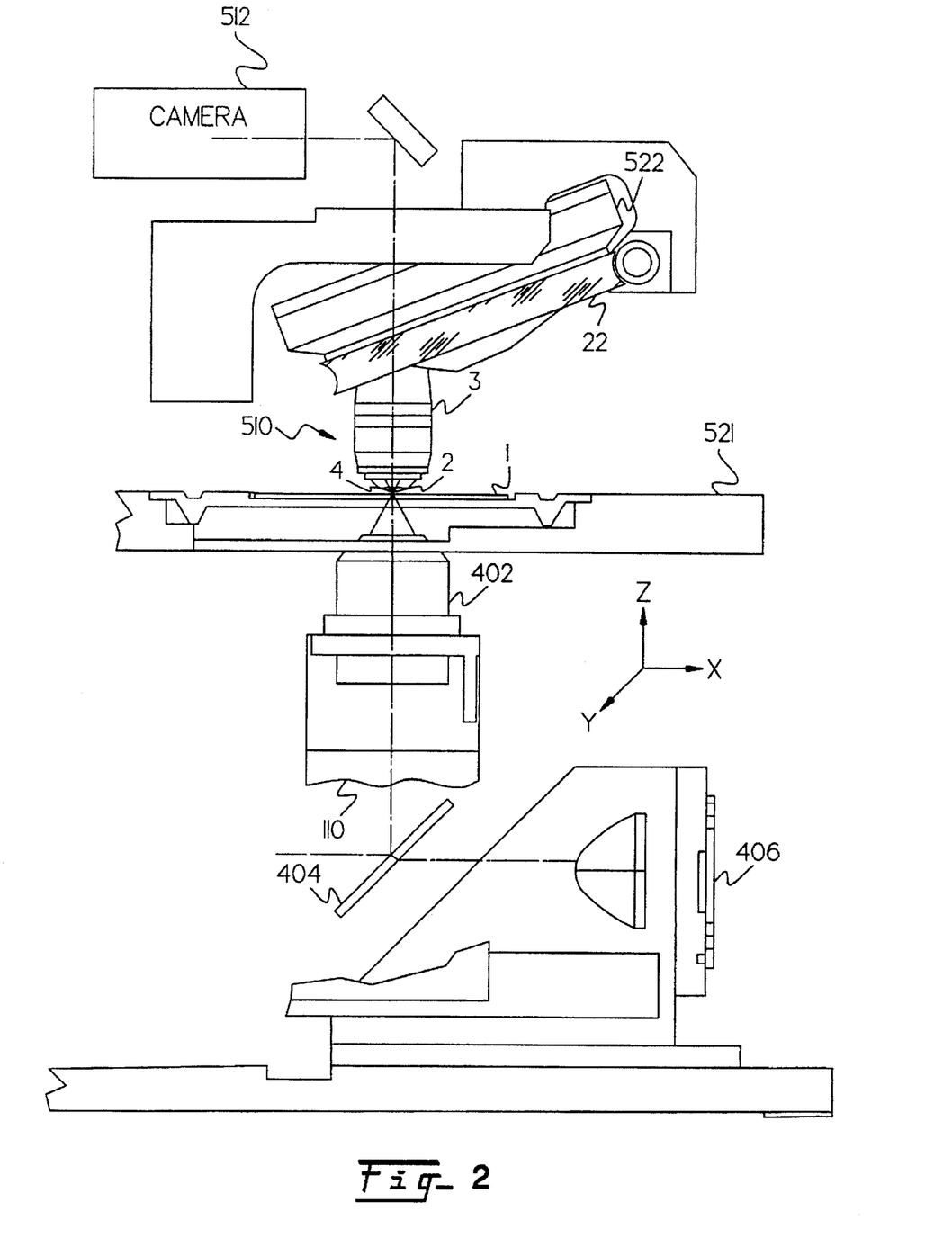
FIG. 2 schematically shows an automated microscope as employed in one embodiment of the invention.

Referring also now to FIG. 2 which shows an automated microscope apparatus, in some embodiments optics 510 may comprise color filters. In one embodiment of the invention, the optics may further comprise an automated microscope 511. The illuminator 508 provides illumination of a slide. The image capture and focus system 516 provides data to a VME bus 538. The VME bus distributes the data to an image processing system 536. The image processing system 536 is comprised of field-of-view processors 568. The images are sent along the image bus 564 from the image capture and focus system 516. A central processor 540 controls the operation of the invention through the VME bus 538. In one embodiment the central processor 562 comprises a MOTOROLA 68030 CPU. The motion controller 504 is comprised of a tray handler 518, a microscope stage controller 520, a microscope tray controller 522, and a calibration slide 524. The motor drivers 526 position the slide under the optics. A bar code reader 528 reads a barcode located on the slide 524. A touch sensor 530 determines whether a slide is under the microscope objectives, and a door interlock 532 prevents operation in case the doors are open. Motion controller 534 controls the motor drivers 526 in response to the central processor 540. An Ethernet communication system 560 communicates to a workstation 542 to provide control of the system. A hard disk 544 is controlled by workstation 550. In one embodiment, workstation 550 may comprise a workstation. A tape drive 546 is connected to the workstation 550 as well as a modem 548, a monitor 552, a keyboard 554, and a mouse pointing device 556. A printer 558 is connected to the Ethernet communication system 560.

During operation, the central computer 540, running a real time operating system, controls the microscope 511 and the processor to acquire and digitize images from the microscope 511. The flatness of the slide may be checked, for example, by contacting the four corners of the slide using a computer controlled touch sensor. The computer 540 also controls the microscope 511 stage to position the specimen under the microscope objective, and from one to fifteen field of view (FOV) processors 568 which receive images under control of the computer 540.

It is to be understood that the various processes described herein may be implemented in software suitable for running on a digital processor such as a commercially available personal computer or other suitable processor. The software may be embedded, for example, in the central processor 540.

Single Image Contrast Quality

Figure 3:
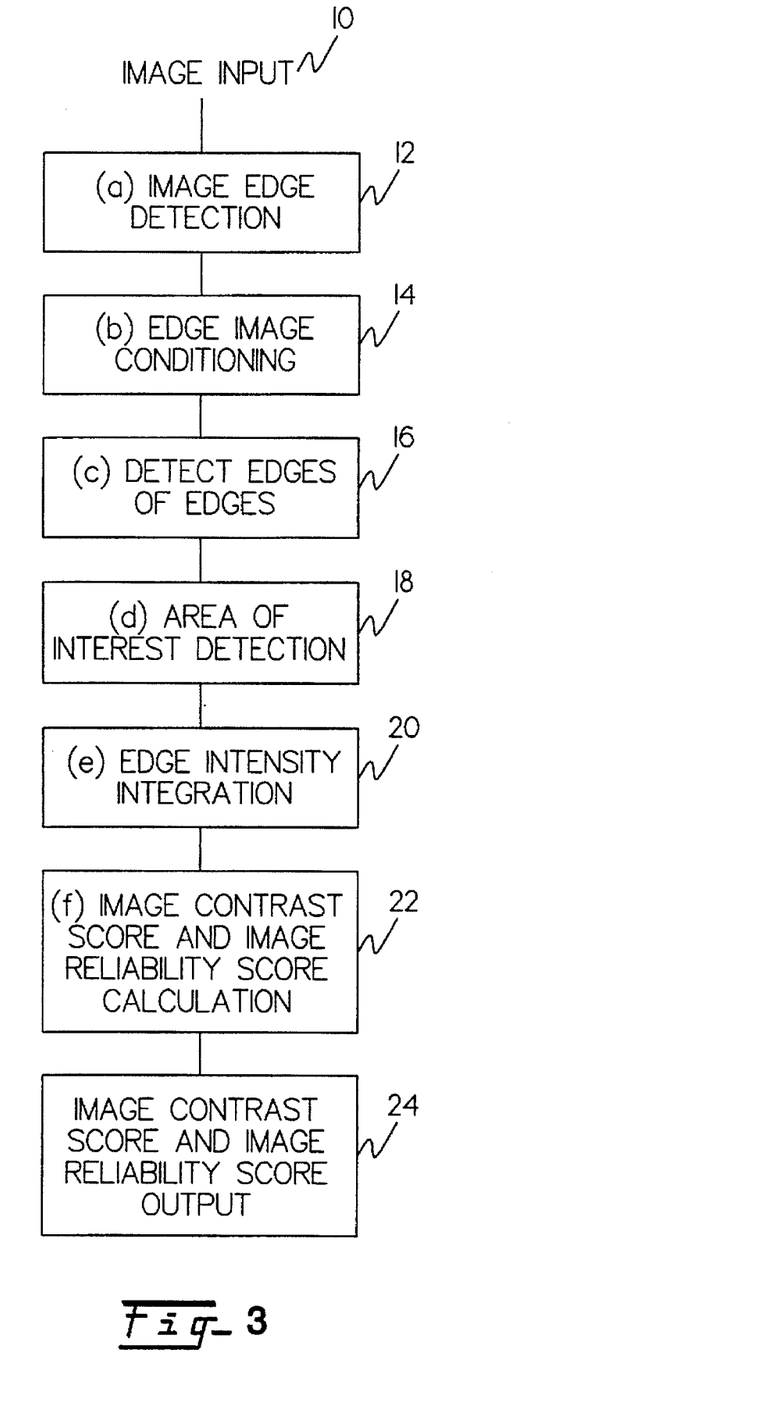
FIG. 3 shows a flow chart of a method for content independent, single image based image contrast quality evaluation.

Now referring to FIG. 3, a flow chart of a method for content independent, single image based image contrast quality evaluation is shown. An image is acquired at step 10. An image edge gradient is detected at step 12. The image edge gradient is conditioned at step 14. At step 16 edges of edges are detected. At step 18 an area of interest is detected. Edge intensity is integrated at step 20. An image contrast score and image reliability score are calculated at step 22 so as to produce an image contrast score and image reliability score output 24.

Image Edge Detection

The edge gradient of the image is detected at step 12. In one embodiment of the invention, morphological operations are used to detect the edge gradient. Simple morphological residue operators are good edge detectors for the detection of dark, bright, or all edges. To detect dark edges, a morphological dilation residue operator is used. To detect bright edges, a morphological erosion residue operator is used. To detect all edges, the detected dark and bright edges are combined. The morphological edge detection operations can be expressed as follows.

Dark Edge Detection $I \oplus B - I$

Bright Edge Detection $I - I \ominus B$

All Edge Detection $MAX(I \oplus B - I, I - I \ominus B)$ where I is the input image; B is the structuring element for the morphological operation; $\oplus$ is the dilation operator; $\ominus$ is the erosion operator; and MAX is the maximal operator.

Edge Image Conditioning

The edge image conditioning step 14 conditions the edge gradient image so that no edge gradient from any object has dominant effect. In one embodiment of the invention, the edge image conditioning step limits the edge gradient value to 60 in a scale of 0 to 255. That is, any edge gradient value greater than 60 will become 60. The operation can be described by the following formula:

$I\_condition = MIN(I\_input, 60)$ where MIN is the minimal operation and I_input is the input image.

Figure 4A:
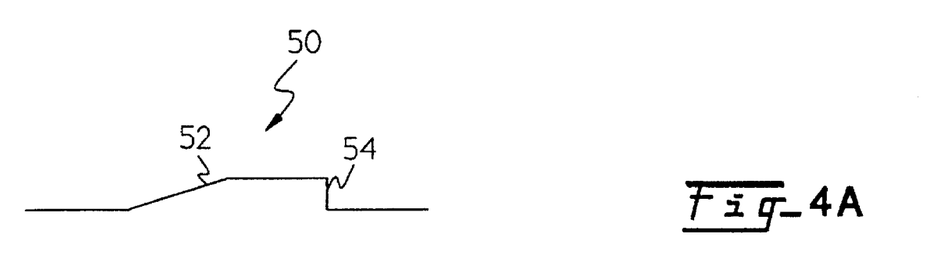
FIGS. 4A, 4B, 4C, 4D, 4E, 4F and 4G schematically show an example of morphological edge detection.

Referring now to FIGS. 4A, 4B, 4C, 4D, 4E, 4F and 4G, an example of morphological edge detection as used in the present invention is shown. FIG. 4A shows a one dimensional image signal 50, including an edge 52 and an edge 54. It will be understood that the image signal may be digitally stored in a digital processor or digital memory and that it is representative of an image in a field of view contained on a slide specimen. Those skilled in the art will recognize that other types of images may be processed by the method of the invention.

Figure 4B:
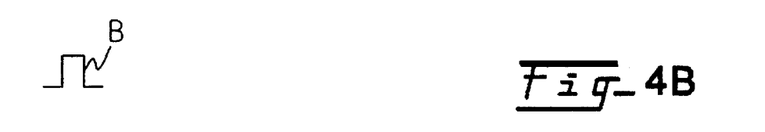
Figure 4C:
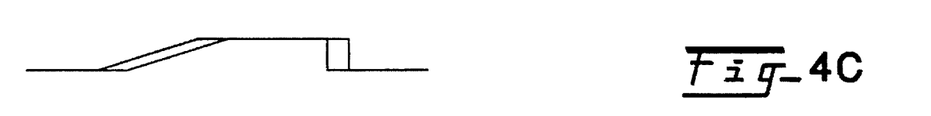

FIG. 4B shows a structure element B. FIG. 4C shows the result of a dilation operation combining image 50 with the structure element B according to the morphological equation:

$$I \oplus B.$$

Figure 4D:
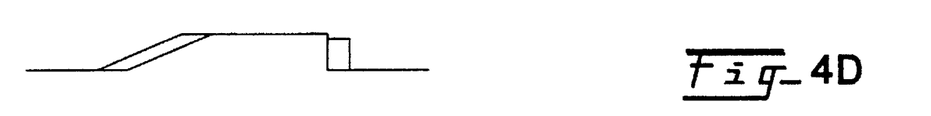

FIG. 4D shows a morphological erosion of structuring element B and image signal 50 according to equation:

$$I \ominus B.$$

Figure 4E:
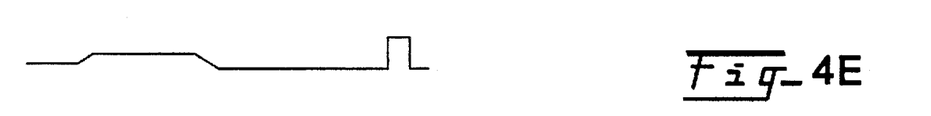

FIG. 4E shows the result of image I subtracted from the morphological dilation operation of FIG. 4C according to the equation:

$$I \oplus B - I.$$

Figure 4F:
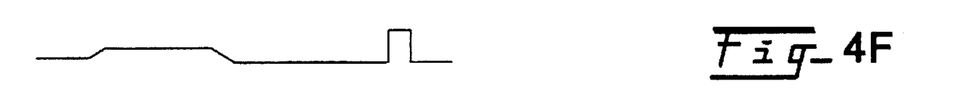

FIG. 4F shows the result of the subtraction of the morphological erosion operation of FIG. 4D subtracted from the image of FIG. 4A according to the equation.

$$I - I \ominus B.$$

Figure 4G:
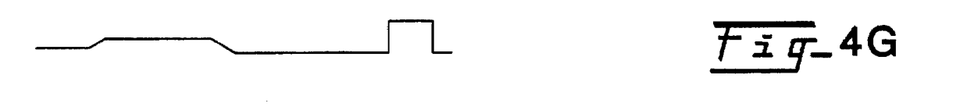

FIG. 4G is a representation of the combination of FIGS. 4E and FIG. 4F according to the morphological equation:

$$MAX(I \oplus B - I, I - I \ominus B).$$

Detect Edges of Edges

Figure 5A:
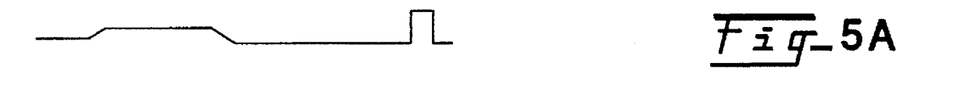
FIGS. 5A, 5B and 5C show an edges of edges detection example as employed in one embodiment of the invention.
Figure 5B:
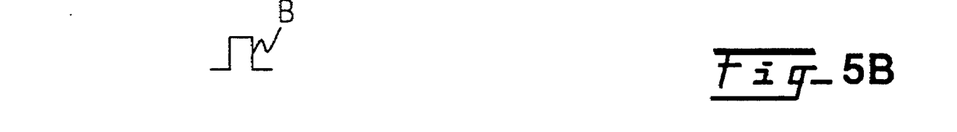
Figure 5C:
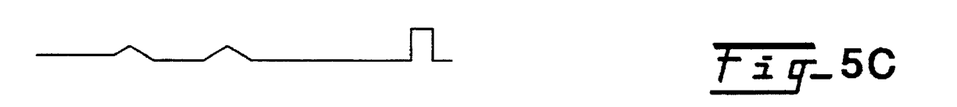

A bright edge detection operation may be applied to the edge gradient image in step 12. FIG. 5C shows the results of an edge erosion residue operator applied to the dark edge results of FIG. 4E. As shown in FIG. 5C, the resulting edge of a high contrast step edge is the same as the original edge signal yet the resulting edge of a lower contrast ramp edge retain only a partial signal of the original edge signal.

Areas of Interest Detection

To further condition the resulting contrast quality evaluations, only the image area having significant objects are considered in the evaluation at step 18. A qualification limit is set based on the magnitude of the edge gradient. If the edge gradient is too low, less than 10 in one embodiment of the invention, the region of the image is excluded from the contrast evaluation. That is:

$$I\_region\_of\_interest = I\_edge >= 10$$

where I_region_of_interest is the image in the region of interest, and I_edge is the edge gradient.

Edge Intensity Integration

To derive the image contrast score of an image, the edge intensity and the edge of edge intensity of the areas of interest are integrated by an accumulation of the intensity values at step 20. Two values are generated as the outcome of this stage, namely, a value of accumulated edge intensity and a value of accumulated edges of edges intensity at step 16.

Image Contrast Score and Image Reliability Score Calculation

At step 22, an image contrast score is defined as the ratio of the accumulated edges of edges intensity to the accumulated edge intensity. The image contrast score may be, for example, a value between 0 and 1.0 with 0 for worst focus and 1 for the best focus. An image reliability score may be defined as the value of accumulated edge intensity. When the image reliability score is low, it is an indication that the image contrast data may be derived from an image with insufficient material for reliable image contrast evaluation.

Processing Quality Evaluation of a Biological Specimen

Figure 6:
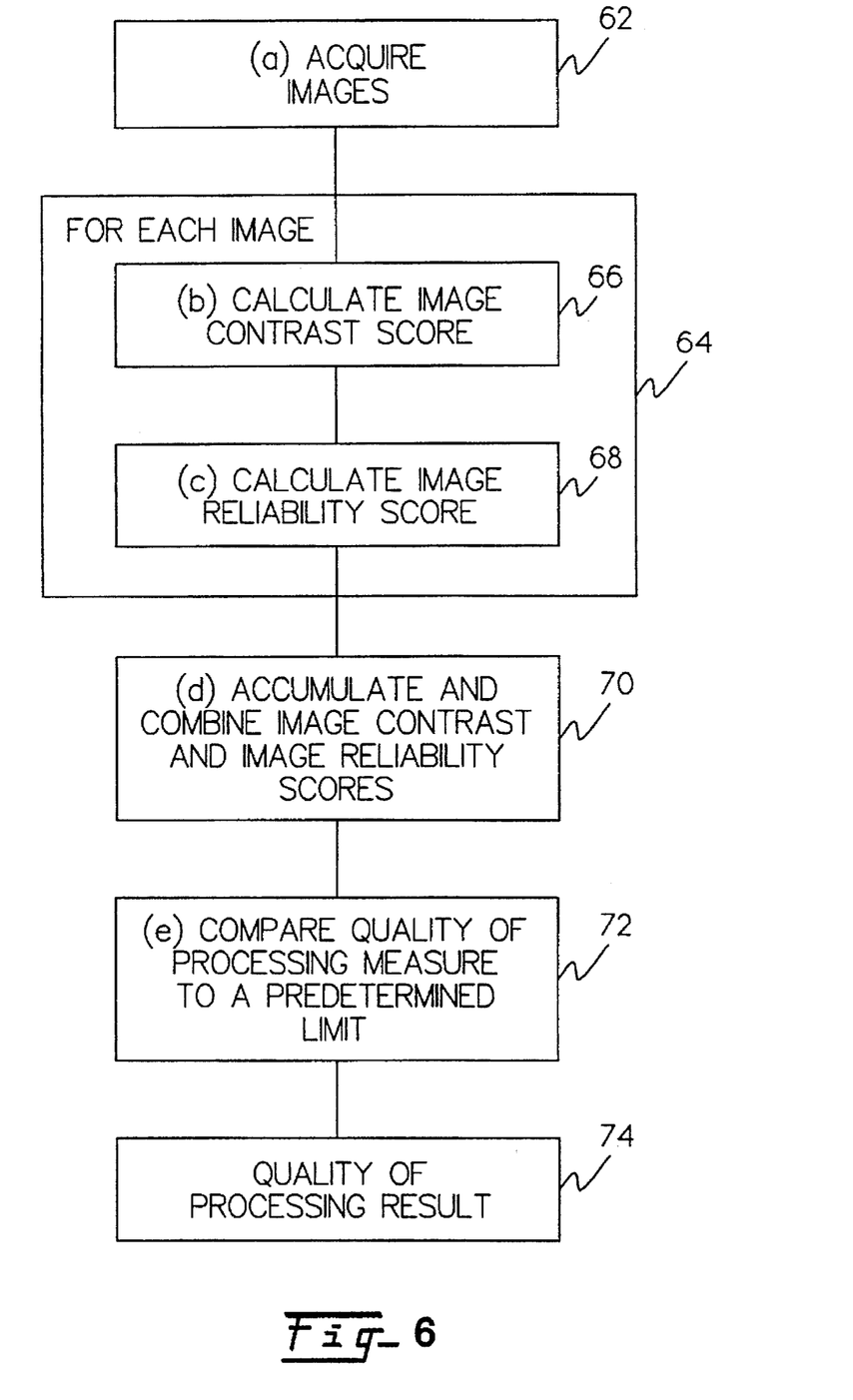
FIG. 6 shows a flow chart of a method for evaluating quality of processing of a specimen as employed in one embodiment of the invention.

Referring now to FIG. 6, a flow chart of a method for evaluating the quality of processing and the overall quality of image focus for a given specimen is shown. The method comprises the following steps:

(a) acquire images for a specimen 62, (b) calculate image contrast score for each image 64, 66, (c) calculate image reliability score for each image 64, 68, (d) accumulate and combine image contrast and image reliability score for a plurality of images of the specimen to calculate a quality of processing measure 70, (e) compare the quality of processing measure to a predetermined limit 72 to produce a quality of processing result 74.

Acquire Images

One example of an image acquisition system is an automated biological screening system such as the one discussed above wherein images of a biological specimen are acquired.

Accumulate and Combine Image Contrast and Image Reliability Scores

In one embodiment of the invention, the image contrast score and the image reliability score for each image are combined to provide a contrast quality score. When the image reliability score is below a first predetermined limit, the contrast quality score is set to a first low value. Otherwise, when the image reliability score is below a second predetermined limit, the contrast quality score is set to a second low value which is higher than the first low value. Otherwise the contrast quality score is the image contrast score which is higher than the first and second low value. The contrast quality score is stored into a predetermined number of bins of a histogram. In one embodiment of the invention, 16 bins are used. A summary statistic, in this case, the mean bin of the contrast quality score, is the quality of processing measure.

Figure 7:
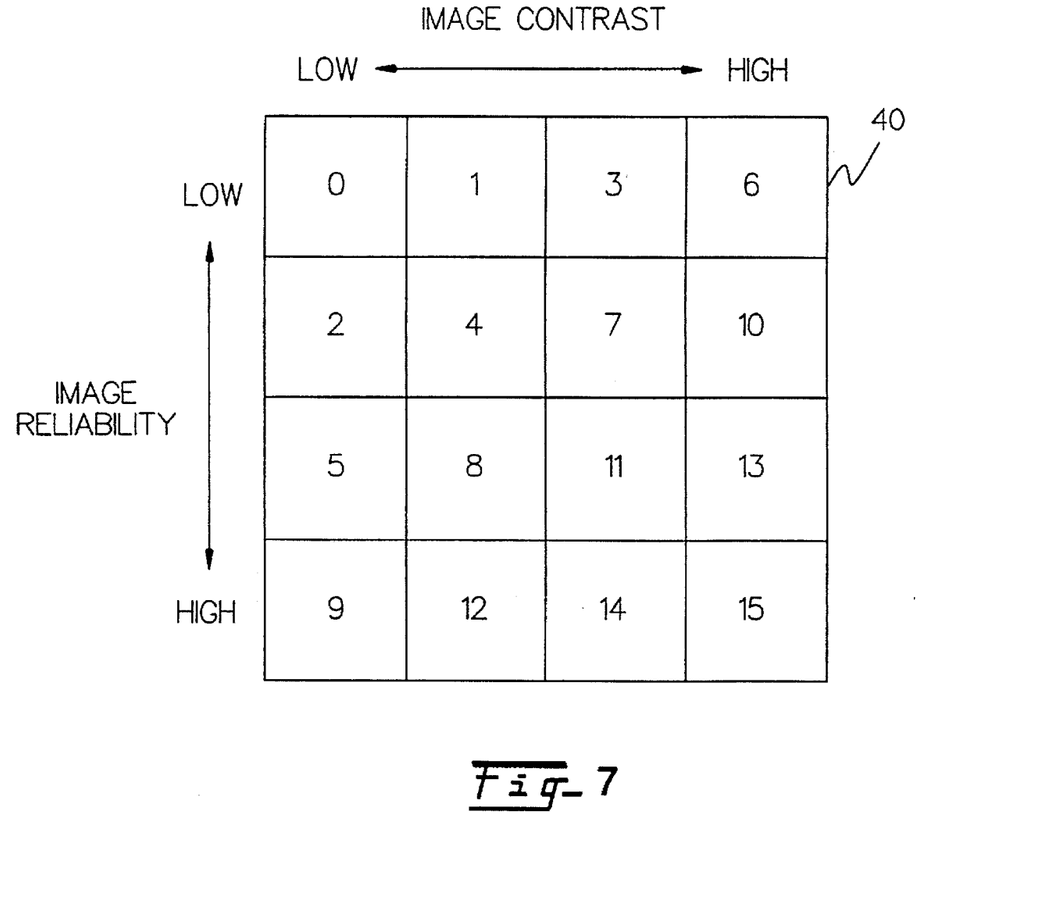
FIG. 7 shows an example of weighting factors for summary statistic calculation for a two dimensional histogram which includes image contrast score and image reliability score values.

Referring now to FIG. 7, an example histogram of image contrast score and image reliability score values is shown. In another embodiment of the invention a two dimensional histogram is used to accumulate image contrast score versus image reliability score from the images of a specimen. A summary statistic of this two dimensional histogram yields the quality of processing measure. In this embodiment of the invention the two dimensional histogram is a 4 by 4 histogram 40. The summary statistic comprises a weighted average of the bins where bin weights are as shown in histogram 40.

Compare Quality of Processing Measure

In the preferred embodiment, if the quality of processing measure is above a predetermined limit, the image contrast of images acquired by the automated biological screening system for the given specimen may be considered as adequate.

The invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A method for measuring the contrast quality of an image comprising the steps of:
   (a) acquiring an image;
   (b) operating on the image to compute a first edge intensity value; and
   (c) operating on the image to compute an edge of edge intensity value; and
   (d) computing an image contrast score for the image as the ratio of the edge of edge intensity value to the first edge intensity value.

2. The method of claim 1 wherein the step of operating on the image to compute a first edge intensity value further comprises the steps of:
   (a) detecting an edge gradient of the single image to produce an edge gradient image; and
   (b) accumulating values of the edge gradient image.

3. The method of claim 2 further comprising the steps of:
   (a) image conditioning the edge gradient image so as to produce a conditioned edge gradient image; and
   (b) processing the conditioned edge gradient image so as to produce an edge of edge image.

4. The method of claim 3 wherein the step of image conditioning the edge gradient image so as to produce a conditioned edge gradient image limits the edge gradient image value to a predetermined minimum limit.

5. The method of claim 3 wherein the step of operating on the image to compute an edge of edge intensity value further comprises computing an accumulated value of the edge of edge image.

6. The method of claim 2 wherein the step of detecting an edge gradient of the single image to produce an edge gradient image comprises a morphological operation.

7. The method of claim 6 wherein the morphological operation comprises applying a dilation residue operator to the image.

8. The method of claim 6 wherein the morphological operation comprises applying an erosion residue operator to the image.

9. The method of claim 6 wherein the morphological operation comprises the step of morphologically combining detected edges.

10. The method of claim 1 further comprising the step of computing an image reliability score for the image derived from the first edge intensity value.

11. The method of claim 10 further comprising the step of comparing the image reliability score to a predetermined limit so as to produce a quality of processing result.

12. The method of claim 10 wherein the image reliability score is low, it is an indication that the image contrast data may be derived from an image with insufficient material for reliable contrast evaluation.

13. The method of claim 10 further comprising the step of combining the image contrast score and image reliability score.

14. A method for contrast quality evaluation of a biological specimen comprising the steps of:
   (a) acquiring at least one image for a specimen;
   (b) computing at least one image contrast score for the at least one image;
   (c) computing at least one image reliability score for the at least one image;
   (d) accumulating and combining the at least one image contrast score and the at least one image reliability score to produce a quality of processing measure; and
   (e) comparing the quality of processing measure to a predetermined limit to produce a quality of processing result.

15. The method of claim 14 wherein the step of accumulating and combining the image contrast score and image reliability score further comprises the steps of:
   (a) accumulating the image contrast score and image reliability score in a histogram; and
   (b) computing a summary statistic of the histogram so as to produce a quality of processing measure.

16. A method for single image based image contrast quality evaluation, comprising the steps of:
   (a) acquiring an image;
   (b) detecting an edge gradient of the image to produce an edge gradient image;
   (c) processing the edge gradient image so as to produce an edge of edges image;
   (d) processing the edge gradient image so as to produce an accumulated edge intensity value;
   (e) processing the edge of edges image so as to produce an accumulated edges of edges intensity value;
   (f) computing an image contrast score for the image wherein the image contrast score comprises a ratio of the accumulated edges of edges intensity value to the accumulated edge intensity value; and
   (g) computing an image reliability score for the image wherein the image reliability score comprises the accumulated edge intensity value; and
   (h) combining the image contrast score and the image reliability score so as to produce a quality of processing measure.

* * * * *